US00PP17449P2

(12) United States Plant Patent
Dümmen

(10) Patent No.: US PP17,449 P2
(45) Date of Patent: Feb. 27, 2007

(54) **NEW GUINEA *IMPATIENS* PLANT NAMED 'DUERILAV'**

(50) Latin Name: *Impatiens hawkeri*
Varietal Denomination: Duerilav

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 15 days.

(21) Appl. No.: 11/171,754

(22) Filed: Jun. 30, 2005

(51) Int. Cl.
*A01H 5/00* (2006.01)

(52) U.S. Cl. ..... Plt./318
(58) Field of Classification Search ..... Plt./318
See application file for complete search history.

(56) References Cited

U.S. PATENT DOCUMENTS

PP9,194 P * 7/1995 Dehan ..... Plt./318
PP13,713 P2 * 4/2003 Hofmann ..... Plt./318

OTHER PUBLICATIONS

UPOV ROM GTITM Computer Database, GTI Jouve Retrieval Software 2006/05 Citation for 'Duerilav'.*

* cited by examiner

*Primary Examiner*—Wendy Haas
(74) *Attorney, Agent, or Firm*—C. A. Whealy

(57) ABSTRACT

A new and distinct cultivar of New Guinea *Impatiens* plant named 'Duerilav', characterized by its upright, rounded and uniform plant habit; vigorous growth habit; dark green-colored leaves; freely branching and freely flowering habit; and purple-colored flowers that are positioned above and beyond the leaves.

1 Drawing Sheet

Botanical denomination: *Impatiens hawkeri.*
Cultivar designation: 'Duerilav'.

BACKGROUND OF THE INVENTION

The present Invention relates to a new and distinct cultivar of New Guinea *Impatiens* plant, botanically known as *Impatiens hawkeri,* and hereinafter referred to by the name 'Duerilav'.

The new *Impatiens* is a product of a planned breeding program conducted by the Inventor in Rheinberg, Germany. The objective of the breeding program is to develop new freely branching New Guinea *Impatiens* cultivars that flower early and have large flowers.

The new *Impatiens* originated from a cross-pollination made by the Inventor in May, 2000 of a proprietary selection of *Impatiens hawkeri* identified as code number 96-441-2, not patented, as the female, or seed parent, with a proprietary selection of *Impatiens hawkeri* identified as code number 96-237-2, not patented, as the male, or pollen parent. The cultivar Duerilav was discovered and selected by the Inventor as a single flowering plant within the progeny of the stated cross-pollination in a controlled environment in Rheinberg, Germany in May, 2003.

Asexual reproduction of the new cultivar by terminal cuttings in Rheinberg, Germany since May, 2003, has shown that the unique features of this new *Impatiens* are stable and reproduced true to type in successive generations.

SUMMARY OF THE INVENTION

The following traits have been repeatedly observed and are determined to be the unique characteristics of 'Duerilav'. These characteristics in combination distinguish 'Duerilav' as a new and distinct *Impatiens* cultivar:

1. Upright, rounded and uniform plant habit.
2. Vigorous growth habit.
3. Dark green-colored leaves.
4. Freely branching and freely flowering habit.
5. Purple-colored flowers that are positioned above and beyond the leaves.

Plants of the new *Impatiens* can be compared to plants of the female parent selection. In side-by-side comparisons conducted in Rheinberg, Germany, plants of the new *Impatiens* differed from plants of the female parent selection in the following characteristics:

1. Plants of the new *Impatiens* were more compact than plants of the female parent selection.
2. Plants of the new *Impatiens* and the female parent selection differed in flower color.

Plants of the new *Impatiens* can be compared to plants of the male parent selection. In side-by-side comparisons conducted in Rheinberg, Germany, plants of the new *Impatiens* differed from plants of the male parent selection in the following characteristics:

1. Plants of the new *Impatiens* were less compact than plants of the male parent selection.
2. Plants of the new *Impatiens* and the male parent selection differed in flower color.

Plants of the new *Impatiens* can also be compared to plants of the cultivar Fisimp 144, disclosed in U.S. Plant Pat. No. 13,713. In side-by-side comparisons conducted in Rheinberg, Germany, plants of the new *Impatiens* differed from plants of the cultivar Fisimp 144 in the following characteristics:

1. Plants of the new *Impatiens* were more vigorous than plants of the cultivar Fisimp 144.
2. Plants of the new *Impatiens* had shorter internodes than plants of the cultivar Fisimp 144.

3. Plants of the new *Impatiens* had smaller leaves with shorter petioles than plants of the cultivar Fisimp 144.
4. Plants of the new *Impatiens* had smaller flowers than plants of the cultivar Fisimp 144.
5. Plants of the new *Impatiens* and the cultivar Fisimp 144 differed slightly in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ from the color values cited in the detailed botanical description which accurately describe the colors of the new *Impatiens*. The photograph comprises a side perspective view of a typical flowering plant of 'Duerilav' grown in a container.

DETAILED BOTANICAL DESCRIPTION

The cultivar Duerilav has not been observed under all possible environmental conditions. The phenotype may vary somewhat with variations in environment such as temperature and light intensity without, however, any variance in genotype.

The aforementioned photograph and following observations and measurements describe plants grown in Rheinberg, Germany during the spring, under commercial practice in a glass-covered greenhouse. Plants were about 16 weeks from cuttings and were grown in 12-cm containers. During the production of the plants, day and night temperatures averaged 18° C. and light levels were about 4,500 lux.

In the following description, color references are made to The Royal Horticultural Society Colour Chart, 1995 Edition, except where general terms of ordinary dictionary significance are used.

Botanical classification: *Impatiens hawkeri* cultivar Duerilav.

Parentage:

*Female parent.*—Proprietary selection of *Impatiens hawkeri* identified as code number 96-441-2, not patented.

*Male parent.*—Proprietary selection of *Impatiens hawkeri* identified as code number 96-237-2, not patented.

Propagation:

*Type cutting.*—Terminal cuttings.

*Time to initiate roots.*—Summer: About 7 days at 22° C. Winter: About 10 days at 22° C.

*Time to produce a rooted cutting.*—Summer: About 18 days at 22° C. Winter: About 25 days at 22° C.

*Root description.*—Fine, fibrous and white in color.

*Rooting habit.*—Freely branching; dense.

Plant description:

*General appearance.*—Upright, rounded and uniform plant habit; freely branching and flowering habit. Vigorous growth habit.

*Crop time.*—From unrooted cuttings, about 16 weeks are required to produce finished flowering plants in 12-cm containers.

*Plant height.*—About 22 cm.

*Plant diameter or spread.*—About 28 cm.

*Lateral branches.*—Quantity per plant: About eight. Length: About 17.3 cm. Diameter: About 9 mm. Internode length: about 4.5 cm. Color: 59A.

*Foliage description.*—Arrangement: Opposite or in whorls. Length: About 11 cm. Width: About 3.25 cm. Shape: Ovate. Apex: Apiculate. Base: Obtuse. Margin: Serrulate with ciliation. Texture, upper and lower surfaces: Smooth, glabrous; leathery. Venation pattern: Pinnate. Color: Developing and fully expanded foliage, upper surface: 147A. Developing and fully expanded foliage, lower surface: 147B. Venation, upper and lower surfaces: 59A.

*Petiole.*—Length: About 2.5 cm. Diameter: About 3 mm. Texture, upper and lower surfaces: Smooth, glabrous. Color, upper and lower surfaces: 59A.

Flower description:

*Flower type and flowering habit.*—Single purple-colored flowers. Flowers rounded and mostly flat. Freely and continuously flowering; usually about eight flowers and flower buds per lateral branch. Flowers positioned above and beyond the foliage and typically face upward or outward. Petals self-cleaning; gynoecium persistent. Flowers not fragrant.

*Flower longevity.*—Flowers last about one week on the plant.

*Flowering season.*—Year-round under greenhouse conditions; in the garden, flowering from spring until fall. Plants begin flowering about eight weeks after planting.

*Flower buds.*—Length: About 1.2 cm. Diameter: About 8 mm. Shape: Ovoid. Color: 59A.

*Flower diameter.*—About 5.2 cm by 5.6 cm.

*Flower depth* (*excluding spur*).—About 1.8 cm.

*Petals.*—Quantity: Five per flower, imbricate. Length: About 3 cm. Width: About 3.5 cm. Shape: Obcordate. Apex: Cordate. Base: Acute. Margin: Entire. Texture, upper and lower surfaces: Smooth, glabrous; satiny. Color: When opening and fully opened, upper surface: 72B; color becoming closer to 72C with development. When opening and fully opened, lower surface: 74B.

*Spur.*—Quantity: One per flower. Length: About 4.8 cm. Diameter: At apex: Less than 1 mm. At flower: About 2.5 mm. Aspect: Curved downward. Color: 46B.

*Peduncles.*—Length: About 5.7 cm. Diameter: About 1 mm. Strength: Moderately strong; flexible. Color: 59A.

*Reproductive organs.*—Androecium: Stamen quantity/arrangement: Five fused at anthers, hooded; filaments free. Anther length: About 5 mm. Anther shape: Oval. Anther color: 57A and 157C. Pollen amount: Abundant. Pollen color: 11D. Gynoecium: Pistil quantity: One per flower. Pistil length: About 5 mm. Stigma color: 145D. Style length: Less than 1 mm. Style color: 145D. Ovary arrangement: Five-celled. Ovary color: 147A.

*Seeds/fruits.*—Seed and fruit development has not been observed.

Disease/pest resistance: Plants of the new *Impatiens* have not been observed to be resistant to pathogens and pests common to *Impatiens*.

Temperature tolerance: Plants of the new *Impatiens* have been observed to be tolerant to temperatures ranging from 8° C. to 35° C.

It is claimed:

1. A new and distinct cultivar of New Guinea *Impatiens* plant named 'Duerilav', as illustrated and described.

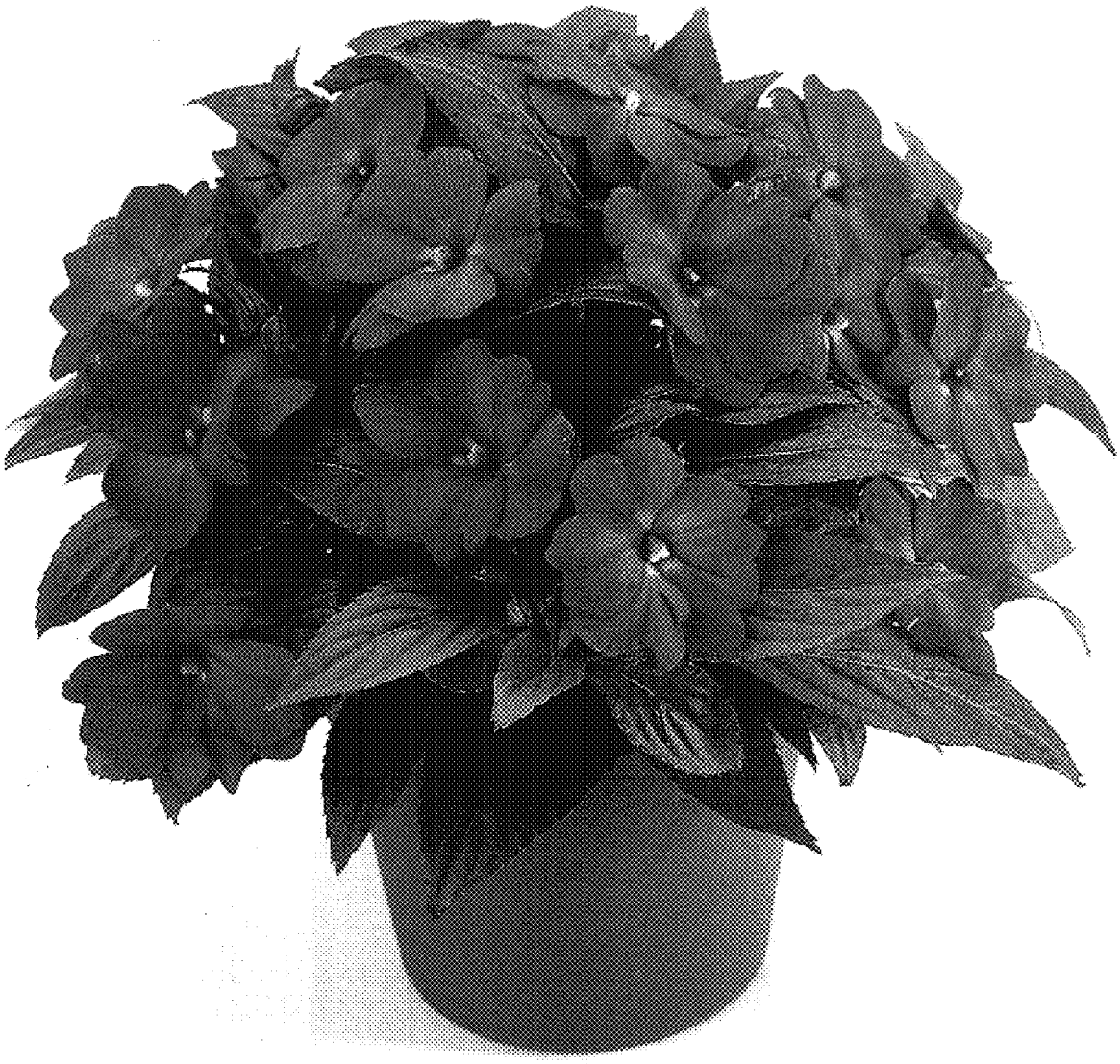

* * * * *